(12) United States Patent
Bastian et al.

(10) Patent No.: US 8,512,345 B2
(45) Date of Patent: Aug. 20, 2013

(54) COMPOUND OFFSET HANDLE

(71) Applicant: Howmedica Osteonics Corp., Mahwah, NJ (US)

(72) Inventors: Adam Bastian, Chester, NY (US); Nicholas Jon LaVigna, Linwood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 13/691,128

(22) Filed: Nov. 30, 2012

(65) Prior Publication Data

US 2013/0090657 A1   Apr. 11, 2013

Related U.S. Application Data

(60) Continuation of application No. 13/041,789, filed on Mar. 7, 2011, now Pat. No. 8,337,502, which is a division of application No. 11/368,761, filed on Mar. 6, 2006, now Pat. No. 7,935,125.

(51) Int. Cl.
| | |
|---|---|
| *A61B 17/00* | (2006.01) |
| *A61B 17/58* | (2006.01) |
| *A61B 17/60* | (2006.01) |
| *A61F 2/46* | (2006.01) |
| *A61F 2/00* | (2006.01) |

(52) U.S. Cl.
USPC ............................. 606/86 R; 606/85; 606/99

(58) Field of Classification Search
USPC ................ 606/84, 85, 86 R, 99, 91, 104, 261
See application file for complete search history.

(56) References Cited

U.S. PATENT DOCUMENTS

| | | |
|---|---|---|
| 3,955,568 A | 5/1976 | Neufeld |
| 4,583,270 A | 4/1986 | Kenna |
| 4,587,964 A | 5/1986 | Walker et al. |

(Continued)

FOREIGN PATENT DOCUMENTS

| | | |
|---|---|---|
| EP | 619097 | 10/1994 |
| EP | 0 645 127 A | 3/1995 |

(Continued)

OTHER PUBLICATIONS

European Search Report, EP 10163915, dated Aug. 18, 2010.

(Continued)

*Primary Examiner* — Sameh Boles
(74) *Attorney, Agent, or Firm* — Lerner, David, Littenberg, Krumholz & Mentlik, LLP

(57) ABSTRACT

A method for preparing a proximal femoral canal of a patient during total hip replacement surgery uses an instrument having a handle, a shaping member including structure configured to shape bone, wherein the structure configured to shape bone comprises at least two cutting surfaces on opposite sides of the shaping member, and a connecting member connecting the handle and the shaping member, the connecting member having a plurality of transverse cross sections. The connecting member includes a dual offset including a first compound bend between the connecting member and the handle, wherein when following a direction from the connecting member to the handle, the first compound bend includes a bend in a posterior direction and a bend in a lateral direction. The connecting member also includes a second compound bend between the connecting member and the shaping member, the second compound bend in an anterior and a medial direction.

1 Claim, 16 Drawing Sheets

(56) References Cited

U.S. PATENT DOCUMENTS

| | | | |
|---|---|---|---|
| 4,765,328 | A | 8/1988 | Keller et al. |
| 4,921,493 | A | 5/1990 | Webb, Jr. et al. |
| 4,990,149 | A | 2/1991 | Fallin |
| 5,089,003 | A | 2/1992 | Fallin et al. |
| 5,190,549 | A | 3/1993 | Miller et al. |
| 5,190,550 | A | 3/1993 | Miller et al. |
| 5,324,293 | A | 6/1994 | Rehmann |
| 5,352,230 | A | 10/1994 | Hood |
| 5,443,471 | A | 8/1995 | Swajger |
| 5,581,892 | A | 12/1996 | Dean |
| 5,810,830 | A | 9/1998 | Noble et al. |
| 5,919,195 | A | 7/1999 | Wilson et al. |
| 5,993,455 | A | 11/1999 | Noble |
| 6,187,006 | B1 | 2/2001 | Keller |
| 6,197,062 | B1 | 3/2001 | Fenlin |
| 6,626,913 | B1 | 9/2003 | McKinnon et al. |
| 7,396,357 | B2 | 7/2008 | Tornier et al. |
| 7,591,821 | B2 | 9/2009 | Kelman |
| 7,935,125 | B2 | 5/2011 | Bastian et al. |
| 8,096,993 | B2 | 1/2012 | Kelman |
| 2003/0220698 | A1 | 11/2003 | Mears |
| 2004/0010261 | A1 | 1/2004 | Hoag |
| 2005/0171548 | A1* | 8/2005 | Kelman .................. 606/79 |
| 2005/0181548 | A1 | 8/2005 | Yanagisawa et al. |
| 2005/0216022 | A1 | 9/2005 | Lechot et al. |
| 2007/0093897 | A1 | 4/2007 | Gerbec et al. |
| 2008/0255565 | A1 | 10/2008 | Fletcher |
| 2010/0121331 | A1 | 5/2010 | Sharp et al. |
| 2011/0247633 | A1 | 10/2011 | Kelman |
| 2011/0295259 | A1 | 12/2011 | Kelman |

FOREIGN PATENT DOCUMENTS

| | | |
|---|---|---|
| FR | 2 742 334 A1 | 6/1997 |
| WO | 00/51530 A1 | 9/2000 |
| WO | 2007050322 A1 | 5/2007 |

OTHER PUBLICATIONS

Kennon, J Bone Joint Surg Am. 2003;85:39-48.

Matta, Hip and Pelvis Institute, St. John's Health Center, The Anterior Approach for Total Hip Arthroplasty: Background and Operative Technique, Aug. 2005.

Zimmer, Inc., The Zimmer Institute Surgical Technique, pp. 33-43, 2006.

* cited by examiner

COMPOUND OFFSET HANDLE

CROSS-REFERENCE TO RELATED APPLICATIONS

This application is a continuation of U.S. application Ser. No. 13/041,789, filed on Mar. 7, 2011, which is a divisional of U.S. application Ser. No. 11/368,761, filed on Mar. 6, 2006, the disclosure of which is incorporated herein by reference.

BACKGROUND OF THE INVENTION

A total or partial hip replacement procedure is sometimes necessary to repair diseased or damaged parts of the hip joint, and in particular, the femoral head or the acetabular cup of the hip joint. During replacement of the femoral head, the diseased or damaged head is removed and the remaining portion of the femur is shaped to receive the stem of an implant which extends into the medullary canal of the bone. A prosthetic, spherical or ball-shaped head is attached to the top of the stem and replicates the anatomy of the removed femoral head, fitting into either the remaining acetabular cup or an artificial replacement therefore.

Shaping of the femoral canal is accomplished using various shaping instruments in the form of femoral rasps or broaches. Generally, such rasps or broaches are designed to match the shape of the stem to be used in the replacement implant so that the femur can be shaped to securely receive the implant. Shaping instruments are inserted into the femoral canal using a handle adapted to affix to the end of the shaping instrument. Many handles have been developed that attach to the proximal portion of shaping instruments for introduction and removal of the shaping instrument from the femur of the patient. However, these handles are designed for use in hip replacement procedures that require either a large incision or a posterior approach in order to gain access to the femur, both of which cause severe trauma to the area surrounding the hip joint increasing the patient's pain and recovery time, and can result in increased risk to the patient.

In an effort to provide a safer, less-traumatic surgical procedure for replacement of the femoral head, it has been determined that an anterior approach to the proximal femur causes less trauma to the surrounding tissue. An anterior approach is already necessary to gain access to the acetabulum for replacement thereof; thus, the ability to take an anterior approach to the femur eliminates the need for a second incision, or a single, large incision. Additionally, an anterior approach requires less muscle dissection compared to a posterior approach. Traditional instrument handles, such as straight or single-plane angled handles, are not conducive to use in hip replacement surgery using an anterior approach because this procedure typically does not allow for straight-line access to the femoral canal, especially when using minimally-invasive surgery (MIS) techniques such as decreased incision size. In particular, problems can arise from the use of traditional handles with respect to alignment of the shaping instrument in the femoral canal, which can cause fracture or misalignment of the femoral implant. Furthermore, problems can arise related to tissue damage from extreme pressure that must be applied to the handle while "fighting" against the tissue for alignment of the shaping instrument within the femoral canal.

Previous attempts at developing an instrument handle for use in minimally invasive surgery have attempted to adapt an instrument handle for use with an incision that does not directly align with the femoral medullary canal. This has resulted in a handle having a "dual offset" design in which the handle incorporates a series of three perpendicular bends to offset the shaping instrument from the proximal section of the handle in both the posterior and lateral directions. This configuration results in a section of the handle that is oriented in the proximal-distal direction, followed by a section that is oriented in the medial-lateral direction, followed next by a section that extends in the anterior-posterior direction, from which the shaping instrument extends in the proximal-distal direction. As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

This type of handle configuration is capable of reaching the femoral medullary canal through an MIS or anterior approach. However, because the handle has two sections that are orthogonal to the direction of movement of the handle, the handle still interferes with the tissue surrounding the femoral medullary canal, resulting in damage thereto. Furthermore, the severity of the bends used in the handle results in a significant loss of linear impaction force from the proximal end of the handle, where the force is applied, to the instrument, where the force acts. This loss in force is due to the tendency of the perpendicular sections to create torque within the handle in both the lateral and anterior directions. While shaping the femoral medullary canal, it is necessary to minimize torque within the shaping handle because such torque is ultimately applied to the bone, which can cause breakage of the bone or misalignment of the implant. At the very least, the loss of the linear force applied to the handle makes it more difficult to shape the medullary canal for acceptance of the implant because the instrument tends to pitch or yaw within the medullary canal.

Therefore, it is desirous to provide a handle for a shaping instrument that allows for the shaping instrument to be introduced through a small incision, preferably on the anterior side of the patient. The handle should allow for proper alignment of the shaping instrument, and adequate linear force transmission, while minimizing damage to surrounding tissue.

During hip replacement surgery, it is often necessary to detach the shaping instrument from its handle. This allows a trial ball-shaped head to be attached to the proximal section of the shaping instrument in a well-known manner for trial reduction of the hip joint. Several variations of such locking mechanisms have been previously developed, but these locking mechanisms are only designed to work with straight or single-plane handles. Therefore, it is also desirous to provide a locking mechanism to attach a shaping instrument to a compound offset handle such that the handle can be easily detached and the handle can be removed from the incision. It is also desirous that this locking mechanism be controlled from the proximal portion of the handle which is located outside of the incision. This prevents the operator from having to reach into the wound to release the handle from or to reattach the handle to the shaping instrument.

Similar advancements are also desired for insertion of the stem portion of an implant into the prepared femoral canal. Preferably, such a device can be used in connection with a minimally invasive or anterior approach to the femoral canal. It is equally important to have accurate control over placement of the implant and adequate force transmission during impaction of the implant as it is with respect to the use of a shaping instrument.

It is therefore, necessary to provide a handle designed for use with a shaping instrument or a femoral implant that can be used in minimally invasive surgery or in surgeries that use an anterior approach to the femoral canal. It is also important for such a device to allow for accurate placement of the instrument or of the femoral implant and accurate and adequate force transmission from the impaction surface to the instrument or stem.

BRIEF SUMMARY OF THE INVENTION

The present invention relates to a device for use on a patient during surgery. The device includes a distal portion, a transition portion, and a proximal portion. The distal portion is adapted to attach to an implement having a proximal portion, an anterior surface and a posterior surface, each surface being spaced apart from a medial-lateral plane through the implement. The transition portion is angled toward an anterior direction and a medial direction with respect to the implement, the proximal portion of the handle being connected to the transition portion and extending in a proximal direction with a medial-lateral plane therethrough substantially parallel to the medial-lateral plane through the implement.

The implement used in connection with the device can be a shaping instrument used in preparing a joint for receiving an implant. The shaping instrument can be used in connection with any joint of the human body, particularly the hip, shoulder, knee or wrist. Most preferably, the shaping instrument includes a femoral rasp or broach used in preparing the proximal femur of the hip joint. Further embodiments of the invention contemplate a device to be used with a joint implant of a portion thereof, including a knee, shoulder or wrist implant, but an implant for replacement of the femoral portion of the hip is preferred.

A further embodiment of the present invention relates to a device for use on a patient during surgery. The device includes a shaping instrument having a proximal portion, an anterior surface, and a posterior surface, each surface being spaced apart from a medial-lateral plane through the shaping instrument, and a handle having a distal portion, a transition portion, and a proximal portion. The proximal portion of the shaping instrument is affixed to the distal portion of the handle, and the transition portion of the handle is angled toward an anterior direction and a medial direction with respect to the shaping instrument. The proximal portion of the handle is connected to the transition portion and extends in a proximal direction with a medial-lateral plane therethrough substantially parallel to the medial-lateral plane through the shaping instrument. The shaping instrument can be either permanently affixed, or integrally formed, with the handle. Preferably, the shaping instrument is removably attached to the handle.

A further embodiment of the present invention includes a method for preparing a proximal femoral canal of a patient during hip replacement surgery. In such a method a device according to one embodiment of the present invention is provided. The device is then inserted into the hip joint through a surgical incision and shaping the proximal femur is shaped with the device. The method further includes removing the instrument from the hip joint.

An alternative embodiment of the present invention includes a method for performing surgery. This method includes providing a device according to a preferred embodiment of the present invention and engaging the distal portion of the device onto a femoral implant. The femoral implant is inserted into the hip joint through a surgical incision and the device is disengaged from the femoral implant. The device is then removed from the surgical incision.

BRIEF DESCRIPTION OF THE DRAWINGS

The present invention will be better understood on reading the following detailed description of nonlimiting embodiments thereof, and on examining the accompanying drawings, in which.

DETAILED DESCRIPTION

In describing the preferred embodiments of the subject matter illustrated and to be described with respect to the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 1:
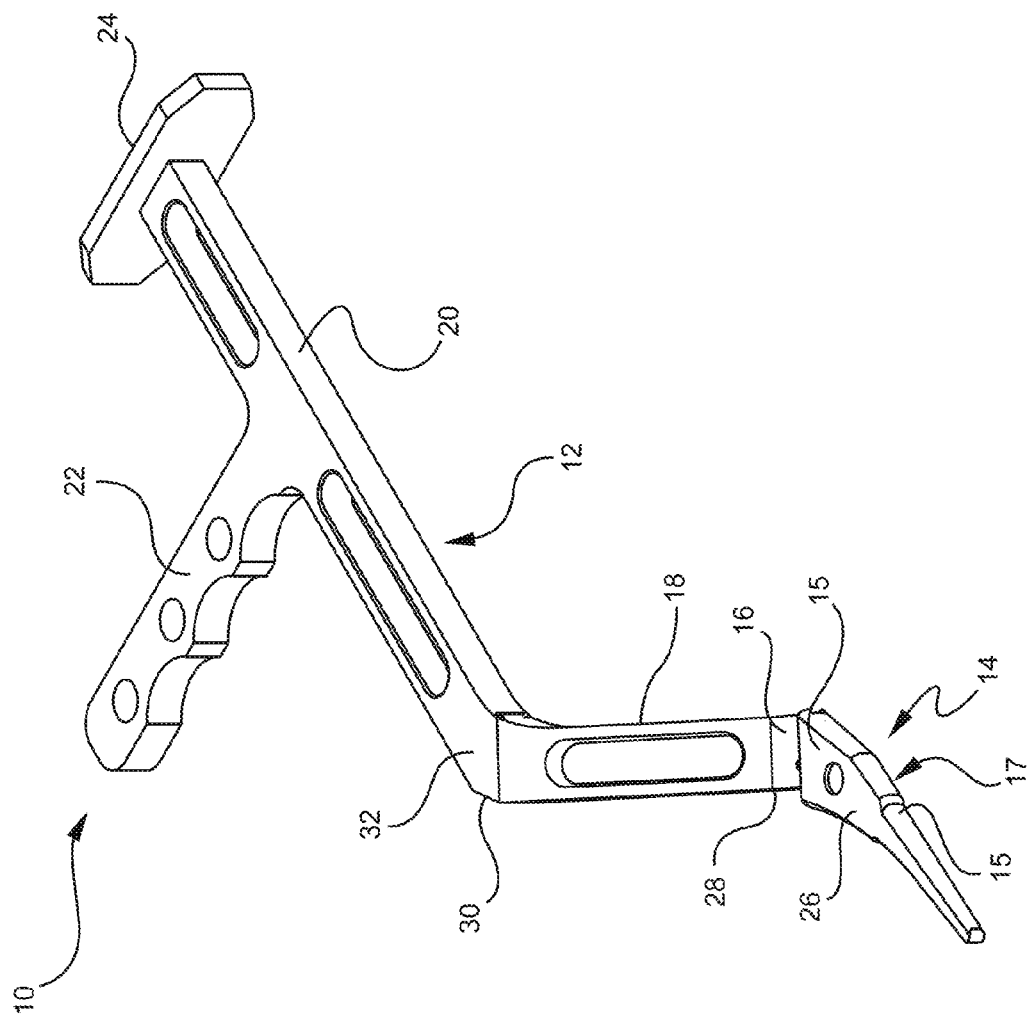
FIG. 1 is a perspective view of a device according to an embodiment of the present invention.
Figure 2:
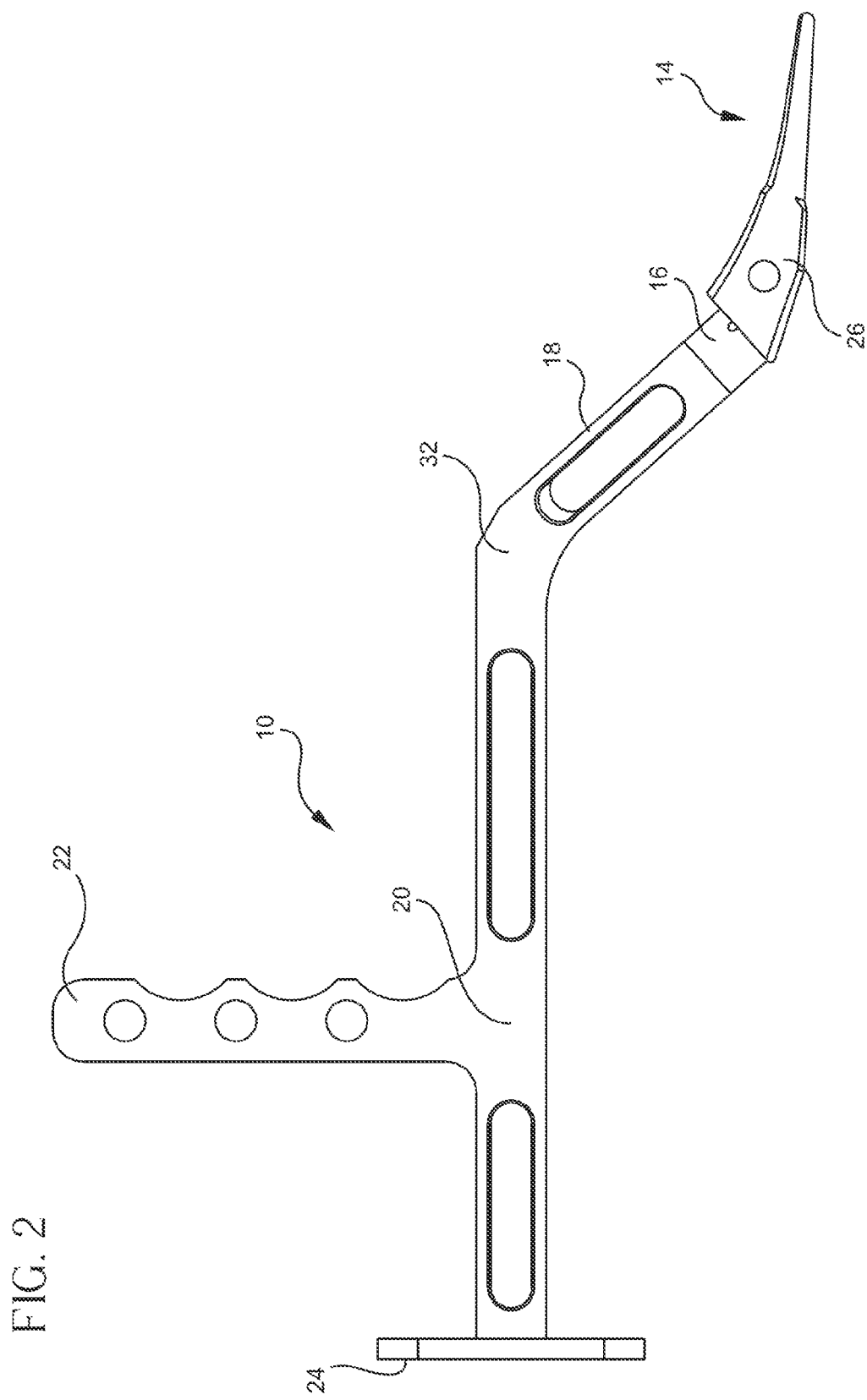
FIG. 2 is a top elevation view of a device according to an embodiment of the present invention.
Figure 3:
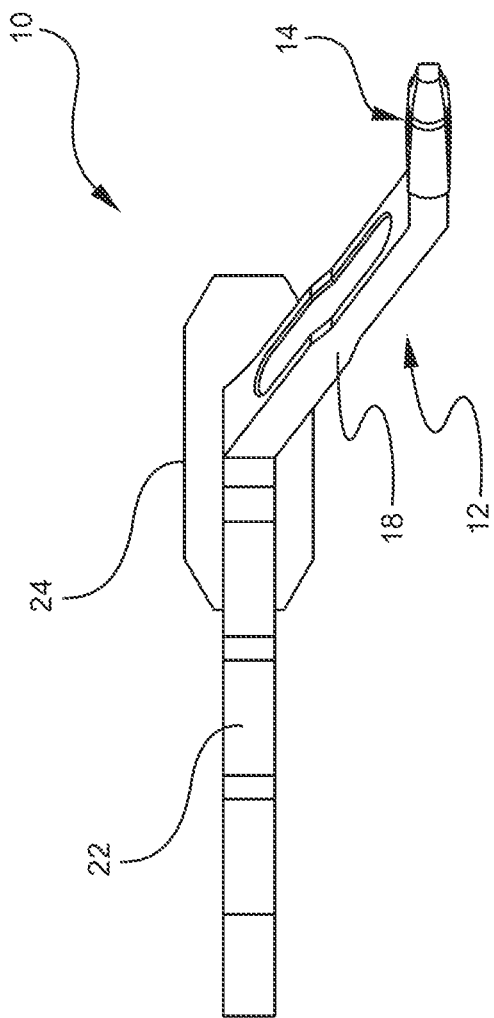
FIG. 3 is a front view of a device according to an embodiment of the present invention.

Referring to the drawings, wherein like reference numerals represent like elements, there is shown in FIG. 1, in accordance with one embodiment of the present invention, a surgical device designated generally by reference numeral 10. In describing preferred embodiments of the device of the present invention, reference will be made to the directional nomenclature used in describing the human body. It is noted that this nomenclature is used only for convenience and that it is not intended to be limiting with respect to the scope or structure of the invention. When referring to specific directions, the device is understood to be described only with respect to its orientation and position during an exemplary application to the human body.

In an embodiment of the present invention, device 10 includes handle 12 and shaping instrument 14. Shaping instrument 14 is of the type typically used in shaping the proximal portion of a femur during hip replacement surgery. Shaping instrument 14 varies in size in accordance with the amount of material to be removed from the femoral canal in order to insert the desired replacement implant. Often, a series of shaping instruments will be used, each successive shaping instrument increasing in size in order to achieve the appropriate shape for the proximal femur.

Generally, shaping instrument 14 has a shape that matches that of the femoral implant that is to be inserted into the femoral medullary canal. Generally, shaping instrument 14 has a width such that it defines a medial-lateral plane through the center thereof. Shaping instrument 14 has two outside surfaces 15 that are substantially parallel to and spaced apart from the medial-lateral plane through the center of shaping instrument 14. These surfaces 15 are formed with a plurality of cutting teeth (not shown) that allow the shaping instrument to remove material from the medullary canal of the proximal femur. Shaping instrument 14 can be in the form of either a femoral rasp or a femoral broach. The design of these devices is generally known in the art.

Handle 12 is divided into a distal section 16, a transition section 18, and a proximal section 20. Handle 12 is made of a material that is sufficiently rigid so as to withstand the force needed to properly align and impact shaping instrument 14 into the femoral medullary canal through use in multiple surgical procedures. Suitable materials for handle 12 are stainless steal, titanium or other similar materials. For ease of use, proximal section 20 may further include a grip 22 or impaction surface 24. Grip 22 allows the user of device 10 to easily hold onto handle 12 during use thereof for purposes of alignment or introduction and removal of shaping instrument 12 with respect to the femoral medullary canal. Impaction surface 24 provides an area on the proximal end 20 of device 10 upon which the handle can be struck with a hammer, mallet or other such device in order to force shaping instrument 14 into the femoral medullary canal. To further aid in impaction of shaping instrument 14 into the femoral medullary canal, handle 12 can be adapted to be used with an automatic impaction device, as it is known in the art.

Handle portion 12 is connected to shaping instrument 14 at distal section 16. Transition section 18 extends from distal section 16 and links distal section 16 to proximal section 20 such that an appropriate compound offset between proximal section 20 and shaping instrument 14 is achieved.

In general, transition section 18 extends from distal section 16 to proximal section 20 so that proximal section 20 is substantially parallel to shaping instrument 14, being offset therefrom in both the anterior and medial directions. Shaping instrument 14 has a longitudinal axis oriented generally in the proximal-distal direction. Similarly, proximal section 20 has a longitudinal axis oriented in the proximal-distal direction, and defines a medial-lateral plane. The distance of the offset in each direction should be such that shaping instrument 14, can be inserted into the femoral medullary canal using a generally anterior approach, while allowing proximal section 20 of handle 12 to be positioned outside of the wound and while minimizing interference with the soft tissue that surrounds the hip joint of the patient. Preferably, proximal section 20 is offset from shaping instrument 14 in the anterior direction by at least 1 inch, but by no more than 3 inches. Similarly, it is preferred that proximal section is offset from the shaping instrument in the medial direction by at least 2 inches, but by no more than 6 inches. Most preferably proximal section is offset from shaping instrument by about 2 inches in the anterior direction and by about 4 inches in the medial direction.

Transition section 18 has a longitudinal axis that is angled relative to the longitudinal axis of shaping instrument 14 in both the medial direction and the anterior direction. Similarly, the longitudinal axis of transition portion 18 is angled relative to the longitudinal axis of proximal section 20 in a posterior direction and a lateral direction. This necessitates the incorporation of a series of bends into device 10. As shown in FIG. 1, medial bend 26 is incorporated into shaping instrument 14. It is also possible to incorporate medial bend 26 in distal section 16 of handle 12. Medial bend 26 is preferably between 30 and 60 degrees, but is most preferably about 45 degrees. Further locations of medial bend 26 would be apparent to those having reasonable skill in the art having read this disclosure.

As further shown in FIG. 1, anterior bend 28 is incorporated into handle 12 at the point where distal section 16 meets transition section 18. Anterior bend 28 is preferably between 15 and 45 degrees, but is most preferably about 30 degrees. Posterior bend 30 and lateral bend 32 are generally positioned at or near the point where transition section 18 meets proximal section 20. Further, posterior bend 30 and lateral bend 32 can be located at approximately the same point in handle 12 forming a compound angle. Preferably, posterior bend 30 is of an angle approximately equal to that of anterior bend 28, and lateral bend 32 is about equal to the angle of medial bend 26, such that the longitudinal axes of proximal section 20 and shaping instrument 14 are approximately parallel.

Figure 4:
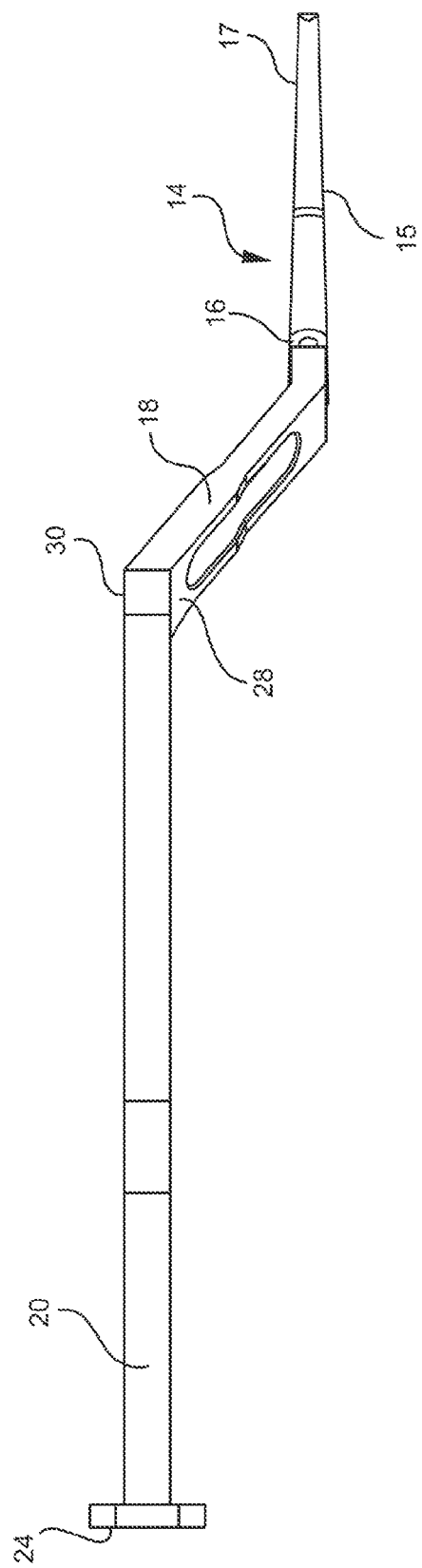
FIG. 4 is a side elevation view of a device according to an embodiment of the present invention.

While shaping instrument 14 and handle 12 can be integrally formed together, it is preferred that shaping instrument 14 is removably attached to handle 12. This arrangement allows different forms of shaping instrument 14, including those of different sizes, to be used with a single handle 12. One form of an attachment mechanism is shown in FIG. 4, wherein threaded hole 35 is formed in distal end 16 of handle 14. A trunion (similar to trunion 46 shown in FIGS. 5 and 6) is attached to proximal end 44 of shaping instrument 14, so as to fit within hole 36 and has notch 48 formed therein. Threaded hole 35 is formed in distal section 16 such that it can engage a set screw and such that it intersects hole 36. Set screw is sized and positioned such that it can be turned within threaded hole 35, advancing the end of set screw through the intersection with hole 36 and into engagement with notch 48. As such, trunion 46 is secured within bore 36, thereby affixing shaping instrument 14 to handle 12.

Figure 5:
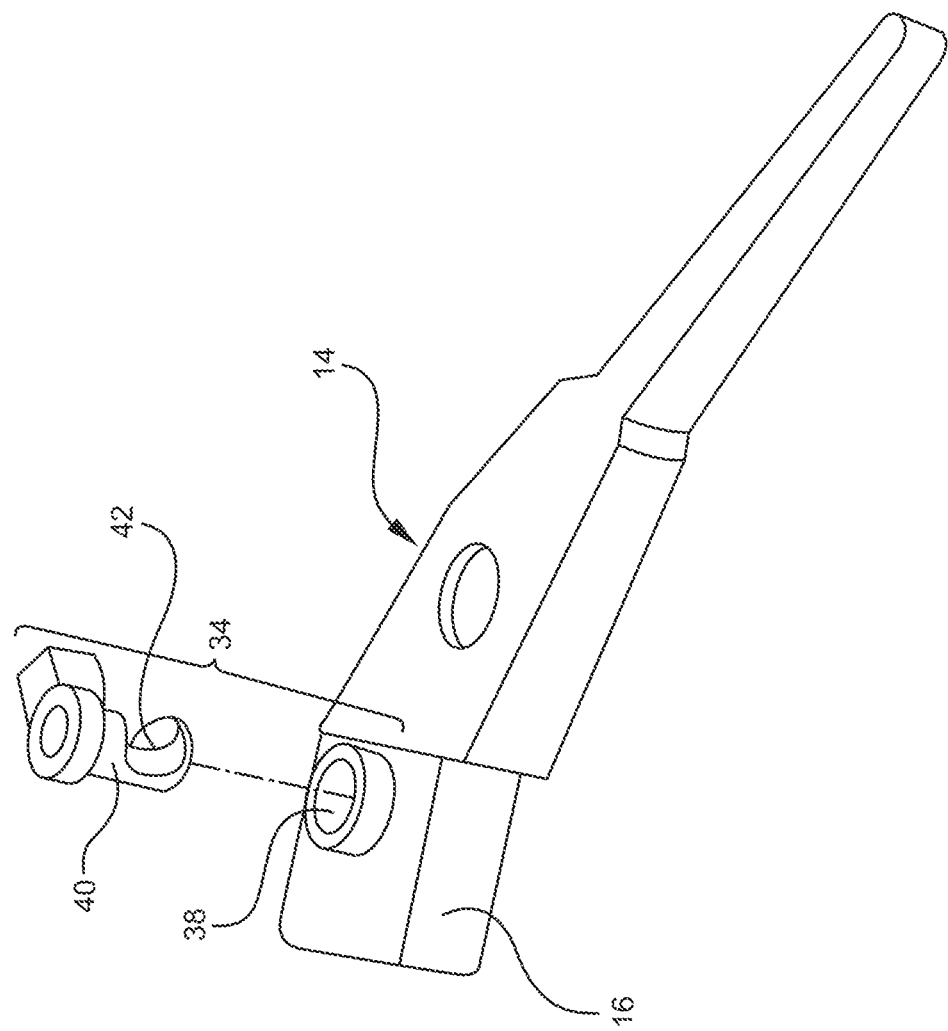
FIG. 5 is a perspective view of an example of an attachment mechanism adapted for use in connection with a device according to an embodiment of the present invention.
Figure 6:
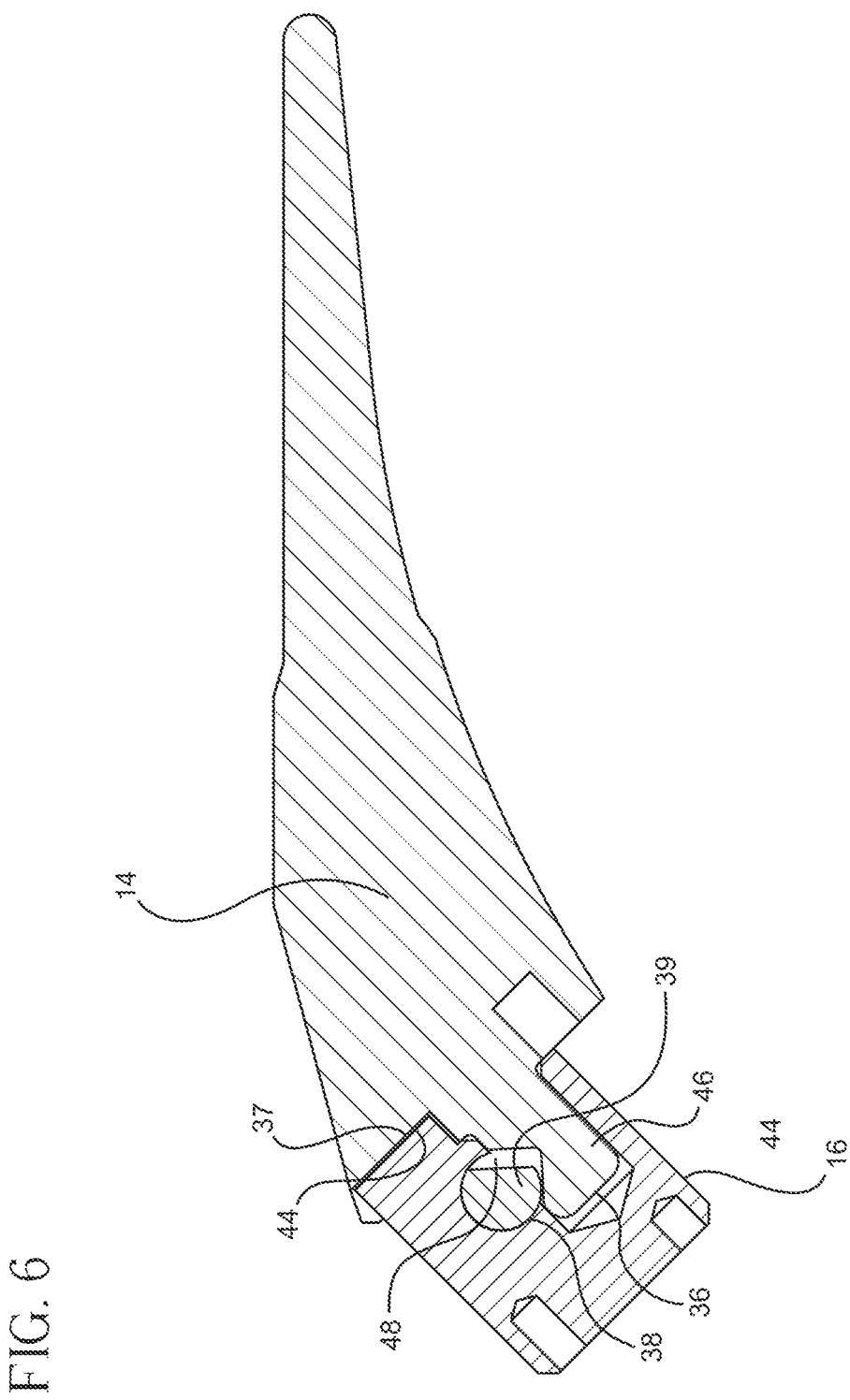
FIG. 6 is a cross-section view of an example of an attachment mechanism adapted for use in connection with a device according to an embodiment of the present invention.

An alternative form of attachment mechanism 34 used for fastening shaping instrument 12 to handle 14 is shown in FIGS. 5 and 6. This type of mechanism 34 is included in distal section 16 of handle 12, and includes first bore 36 in distal section 16 of handle 12 extending from attachment surface 37 of handle 12 in a direction orthogonal thereto. Distal section 16 further includes a second bore 38 running from the posterior surface of distal section 16 to the anterior surface thereof in a direction orthogonal thereto. Second bore 38 is positioned within distal section 16 to form an intersection 39 with first bore 36. Cam 40 is inserted into second bore 38 and has an undercut 42 formed therein. The proximal end of rasp 44 includes a trunion 46 having a notch 48 formed therein. Cam 40 is rotatable within second hole 38 such that it is positionable either in an open position or a closed position. The open position is such that undercut 42 of cam 40 is positioned such that cam 40 does not extend through intersection 39 into first bore 46. The closed position is such that undercut 42 is turned away from intersection 39, such that cam 40 extends through the intersection 39 and into first hole 36.

When cam 40 is in the open position, trunion 46 may freely pass into and out of first bore 36. When handle 12 and shaping instrument 14 are assembled together, trunion 46 is inserted into first bore 36 and cam 40 is rotated into the closed position. In the closed position, a portion of cam 40 extends into first bore 36 and engages notch 48 of trunion 46, such that trunion 46 is secured within second bore 36. This results in shaping instrument 14 being secured to handle 12. In order to aid in securing shaping instrument 14 to handle 12, attachment surface 37 of handle 12 can include a projection 44 that mates with an opening in the proximal end of the shaping instrument 14. This arrangement prevents rotational movement of shaping instrument 14 with respect to handle 12.

Figure 7:
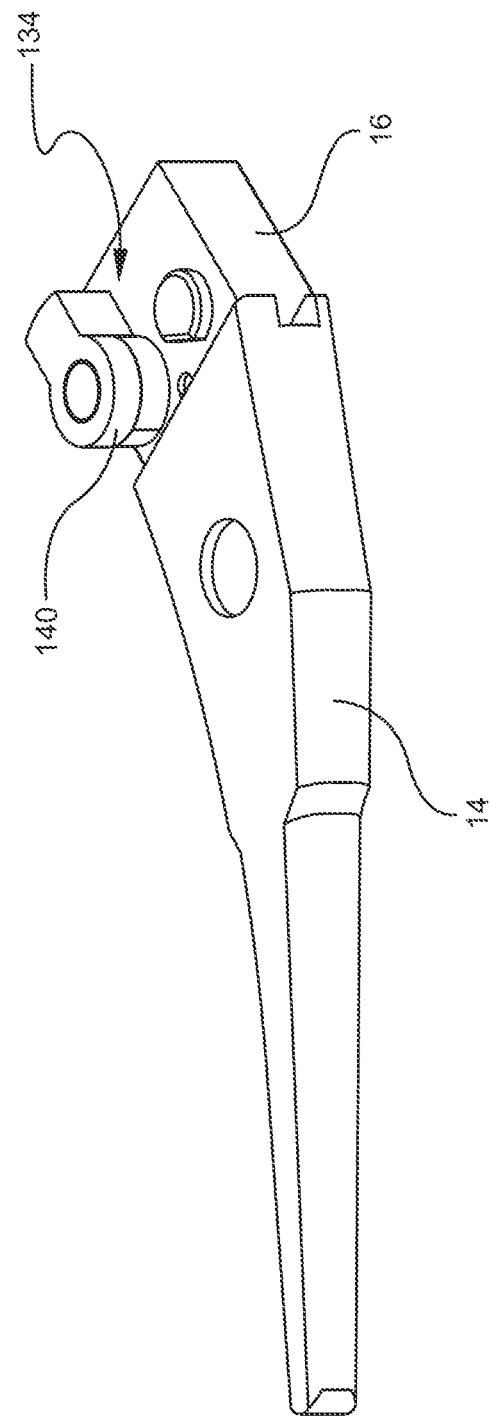
FIG. 7 is a perspective view of an attachment mechanism according to an embodiment of the present invention.
Figure 8:
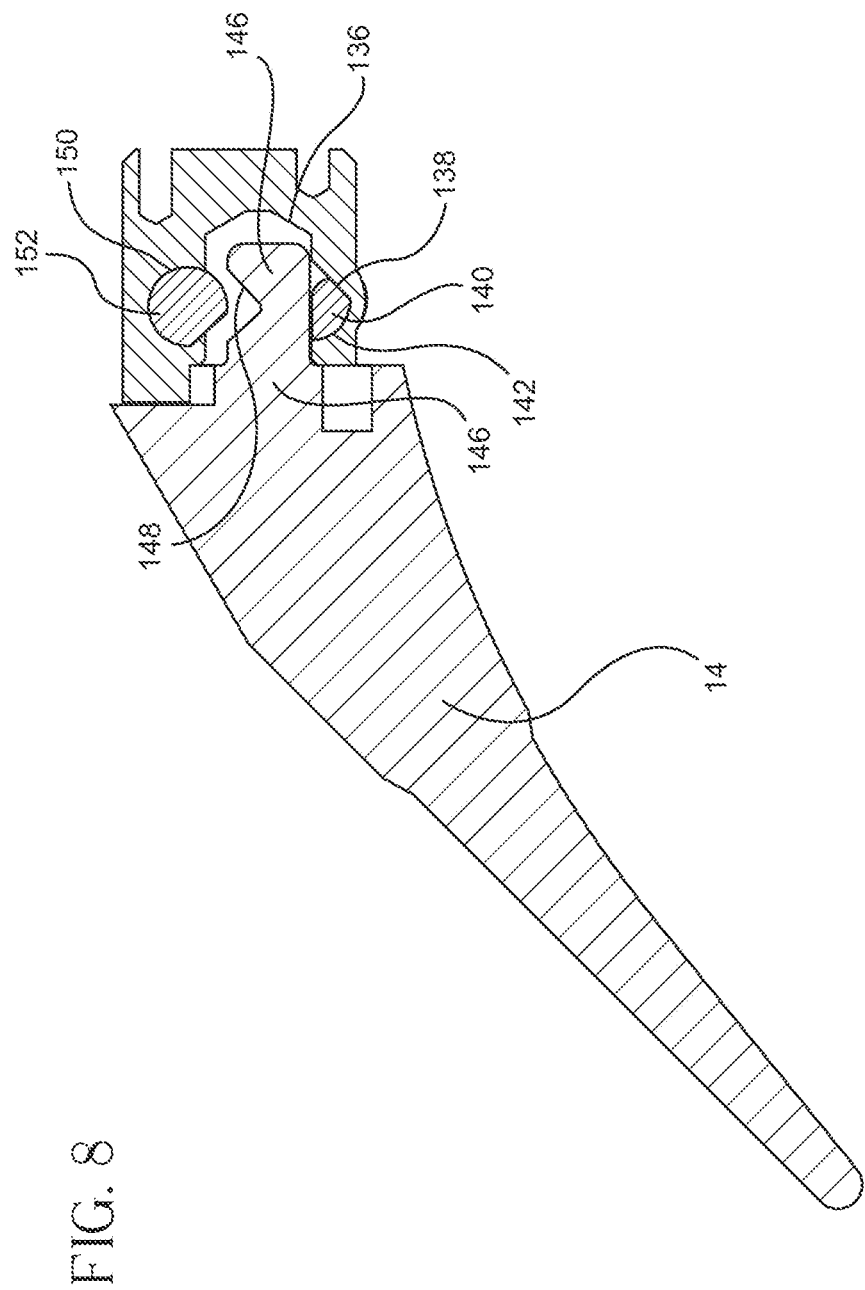
FIG. 8 is a cross-section view of an attachment mechanism adapted for use with a device according to an embodiment of the present invention.
Figure 9:
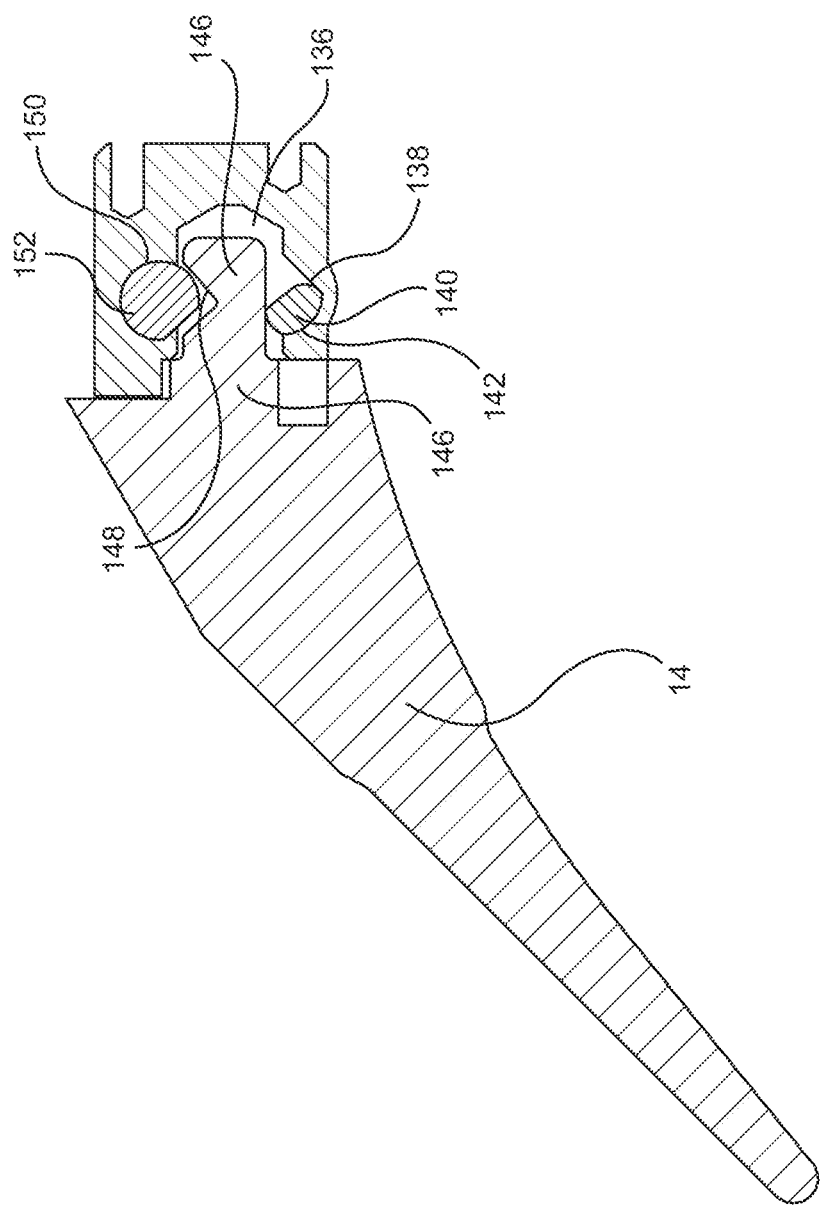
FIG. 9 is a cross-section view of an example of an attachment mechanism adapted for use in connection with a device according to an embodiment of the present invention.

Referring now to FIGS. 7-9, an alternative variation of attachment mechanism 134 is shown. Attachment mechanism 134 includes slot 136 formed in distal section 16 of handle 12 that mates with trunion 46 formed on the proximal portion 44 of shaping instrument 14. Distal portion 16 of handle 12 further includes a bore 138 formed between and orthogonal to the anterior and posterior surfaces of distal section 16. Second bore 138 is positioned such that it intersects the medial side of slot 136. Cam 140, having undercut 142, is positioned in bore 138 such that it is rotatable between an open position and a closed position. In the open position, undercut 42 of cam 40 is oriented such that cam 40 does not extend through the intersection of bore 138 and slot 136. The closed position is such that the undercut is turned away from the intersection, and the body of cam 140 extends through the intersection and into a portion of slot 136. Third bore 150 is formed parallel to bore 138 such that it forms an intersection with the lateral end of slot 136. Third bore 150 has a fixed post 152 secured therein that extends into a portion of slot 136. When cam 140 is in the open position, trunion 146 allows cam 140 to freely pass in and out of slot 136. To allow trunion 146 to be freely moveable in and out of slot 136 when cam is in the open position, slot 136 should have a length sufficient to allow trunion to clear post 152. When cam 140 is rotated into the closed position, cam 140 pushes trunion 146 toward the medial end of slot 136 such that notch 148 formed in trunion 146 mates with post 152, thereby securing trunion 146 within slot 136, and thus, securing shaping instrument 14 to distal section 16.

Figure 10:
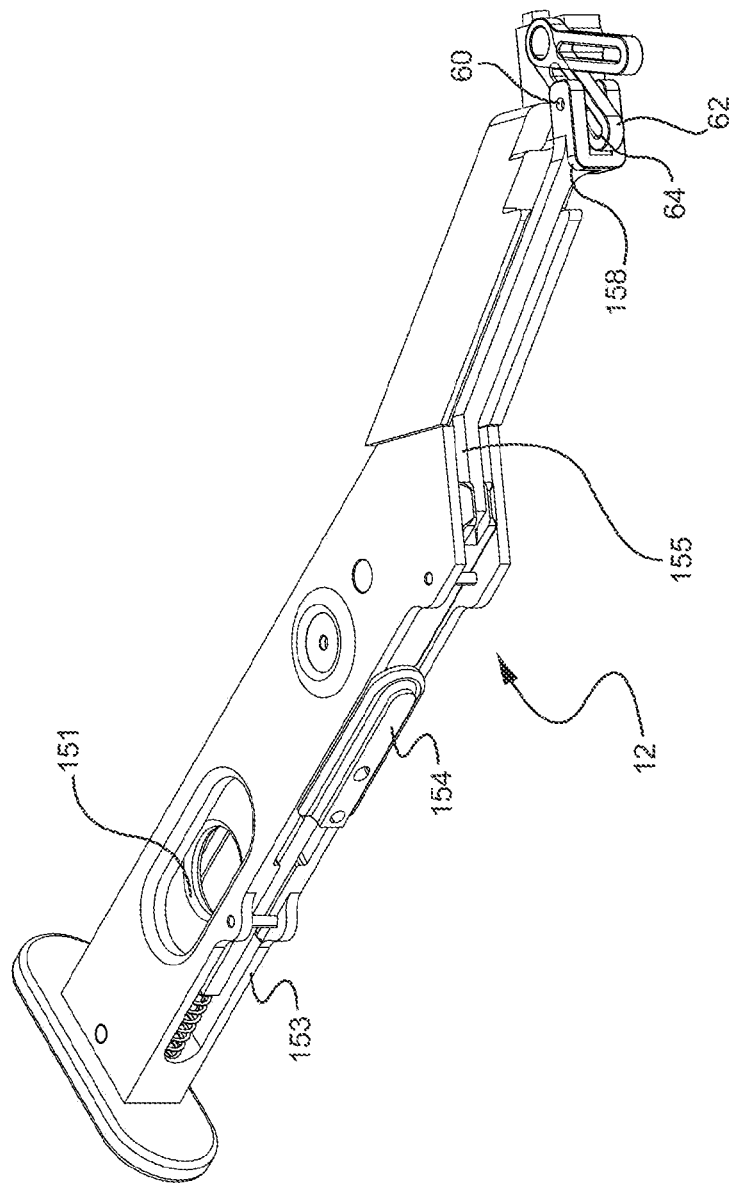
FIG. 10 is an example of a control mechanism adapted for use with a device according to an embodiment of the present invention.
Figure 11:
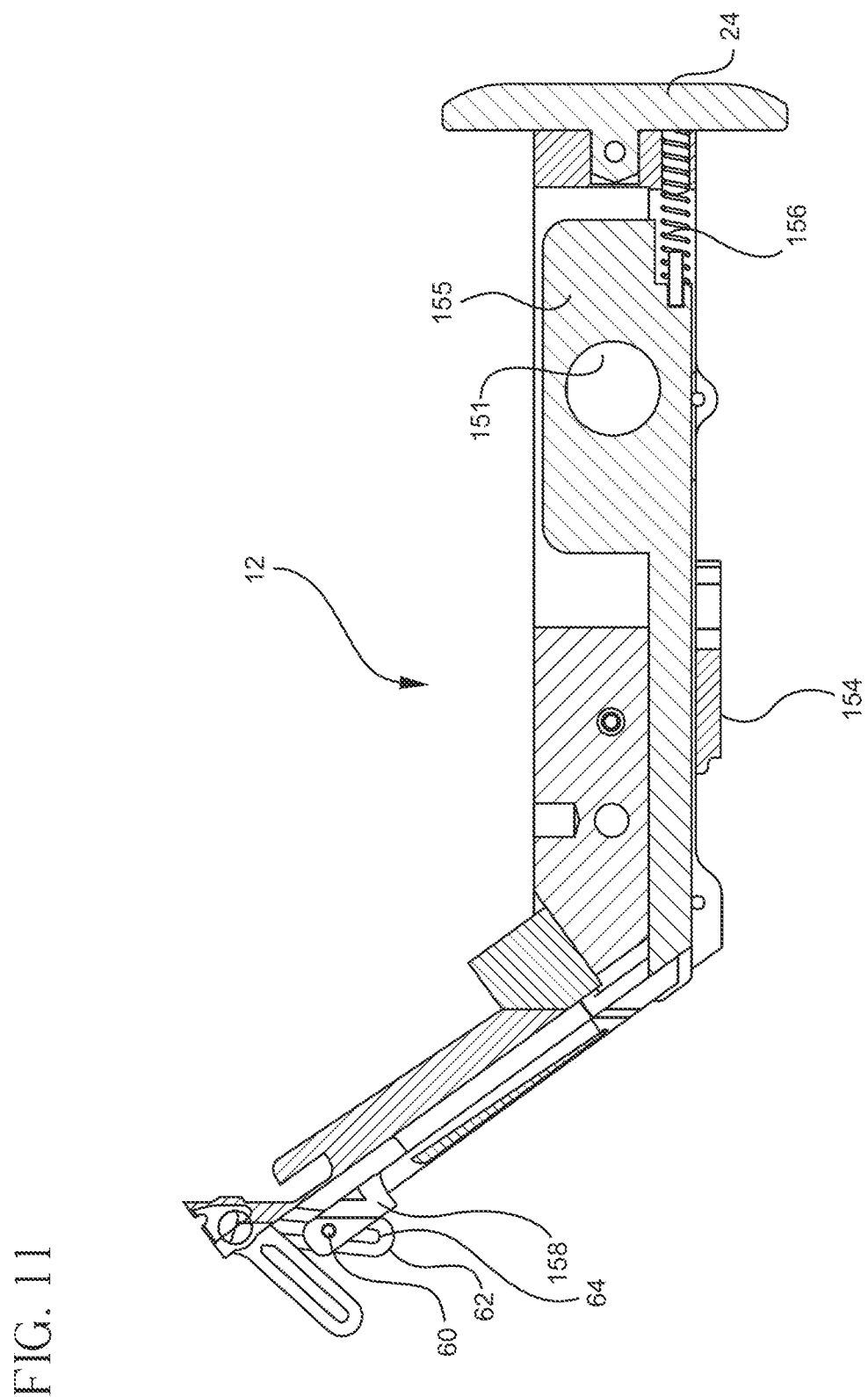
FIG. 11 is a cross-section view of a control mechanism adapted for use in connection with a device according to an embodiment of the present invention.

In order for the user of device 10 to detach and reattach shaping instrument 14 from handle 12 without the need to physically reach into the incision in the patient through which device 10 is inserted, a control means is provided in conjunction with handle 12. An example of such control means is shown in FIGS. 10 and 11. Handle 12 has a generally hollow structure defining cavity 153 therein. Within cavity 153 there is included slide member 155 that is slideable in the proximal-distal direction. Plate 154 is affixed to the outside surface of the handle 12 on the lateral section thereof in order to secure slide member 155 within cavity 153. The proximal end of spring 156 is attached to the proximal end of handle 12, and the distal end of spring 156 is attached to slide member 155 such that it urges slide member 155 toward the proximal end 24 of handle 12. The distal end of slide member 155 includes a fork 158, which is attached using pin 60 to slot 62 formed in lever 64 that is attached to cam 40 extending from bore 38 to the outside of distal section 16. In this mechanism, when slide member 155 is in its natural position, toward the proximal end of handle 12, cam 40 is forced into the closed position. When the user of the device 10 slides slide member 155 toward the distal end of handle 12 using trigger 151, pin 60 secured within fork 158 pushes forward on lever 64 causing cam 40 to rotate into its open position.

Due to positioning of the elements of connection mechanism within distal section 16 of handle 12, it may be necessary to provide a slide member 155 that urges cam 40 into the open position by sliding in the proximal direction. If this is necessary, spring 156 will be such that it urges slide member 155 in the distal direction.

Figure 12:
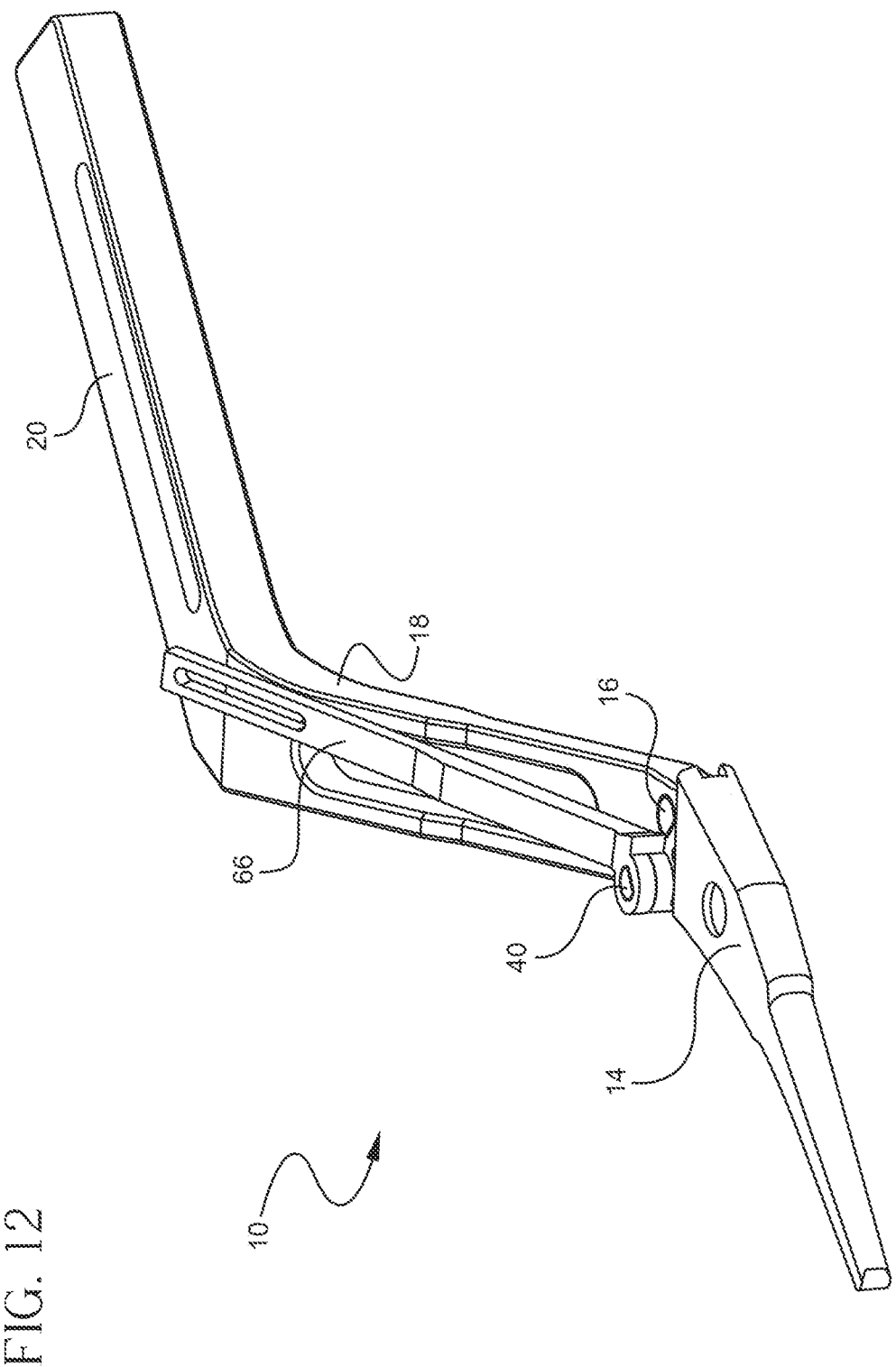
FIG. 12 is a perspective view of a control mechanism adapted for use in connection with a device according to an embodiment of the present invention.

An alternative control mechanism is shown in FIG. 12, in which cam 40 is affixed to an elongated lever 66 that extends along transition portion 18 of handle 12 generally in the proximal direction. To selectively control the rotation of cam as between the open and closed positions the user rotates lever 66 in the appropriate direction.

Figure 13:
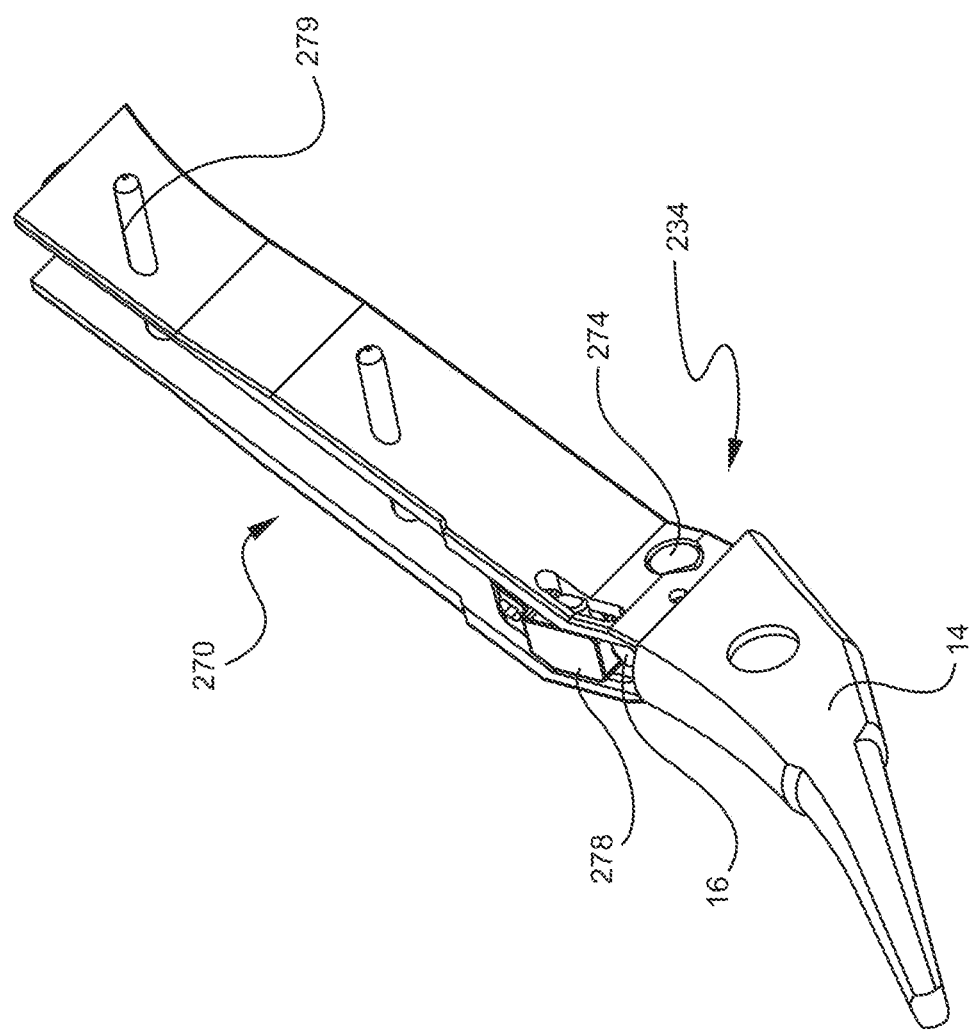
FIG. 13 is a connection mechanism adapted for use with a device according to an embodiment of the present invention.
Figure 14:
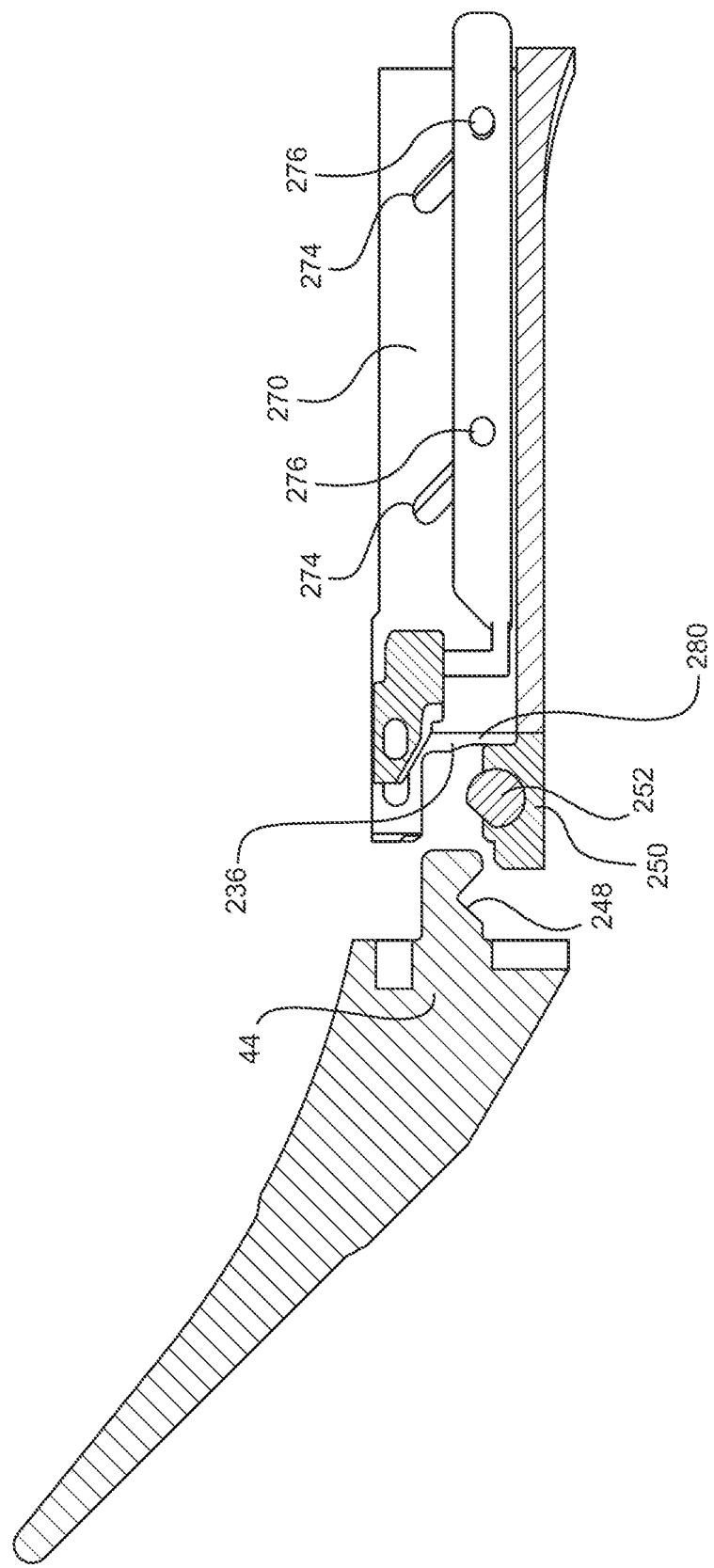
FIG. 14 is a cross-section view of a connection mechanism adapted for use with a device according to an embodiment of the present invention.

In FIGS. 13 and 14 there is shown an alternative attachment mechanism 234 for removably affixing shaping instrument 14 to handle 12. This attachment mechanism 234 includes a slot 236 formed in distal section 16 of handle 12 that is oriented orthogonally with respect to the attachment surface 37 of handle 12. Slot 236 is adapted to engage trunion 246 which is affixed to proximal section 44 of rasp 14. Distal section 16 of handle 12 includes bore 250 that has a fixed post 252 secured therein that is adapted to engage notch 248 formed in trunion 246. Cavity 270 is formed in transition section 18 and distal section 16 of handle 12 and two corresponding sets of slots 274 are formed through the outside wall of transition section 18 to provide access to cavity 270.

Slots 274 are preferably generally oriented at approximately a forty-five degree angle with respect to the longitudinal axis of transition portion 18. This results in slots 274 being oriented approximately in the anterior-posterior direction. Slots 274 and are adapted to engage pins 276, which are affixed to arm 272 disposed in cavity 270, such that pins 276 lie on an anterior-posterior plane. Pins 276 are affixed to and provide support for arm 272 which has hook section 280 formed thereon. Hook section 280 is slideably engaged with wedge 278 which is slideably mounted in cavity 270 such that it can be slid into and out from the intersection formed between cavity 270 and the proximal end of slot 236. In operation, trunion 246 is inserted into slot 236 at the end nearest wedge 278 such that proximal end 44 of rasp 14 contacts attachment surface 37 of handle 12. Pins 276 are then slid in the posterior direction, forcing arm 272 to move within cavity in the same direction such that it exerts a force on wedge 278. The slideable engagement between wedge and hook section 280 of arm 272 allows wedge 278 to move within cavity 270 toward distal end of handle, thereby pushing trunion 246 toward and into engagement with post 252 such that trunion 246 is secured within slot 236. Attachment mechanism 234 is secured in the closed position by the friction generated between all of the moving parts of this arrangement, in particular between pins 276 and slots 274 and between hook section 280 and wedge 278.

Figure 15:
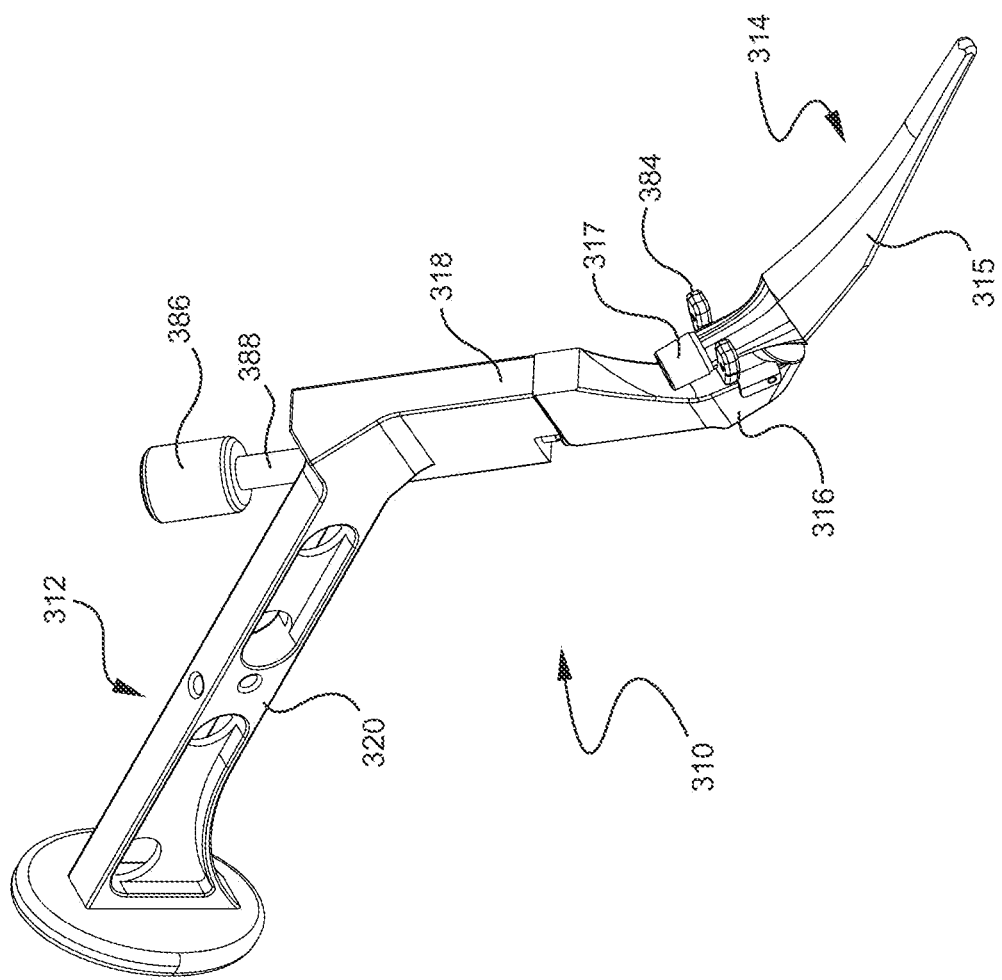
FIG. 15 is a perspective view of a device according to an embodiment of the present invention.
Figure 16:
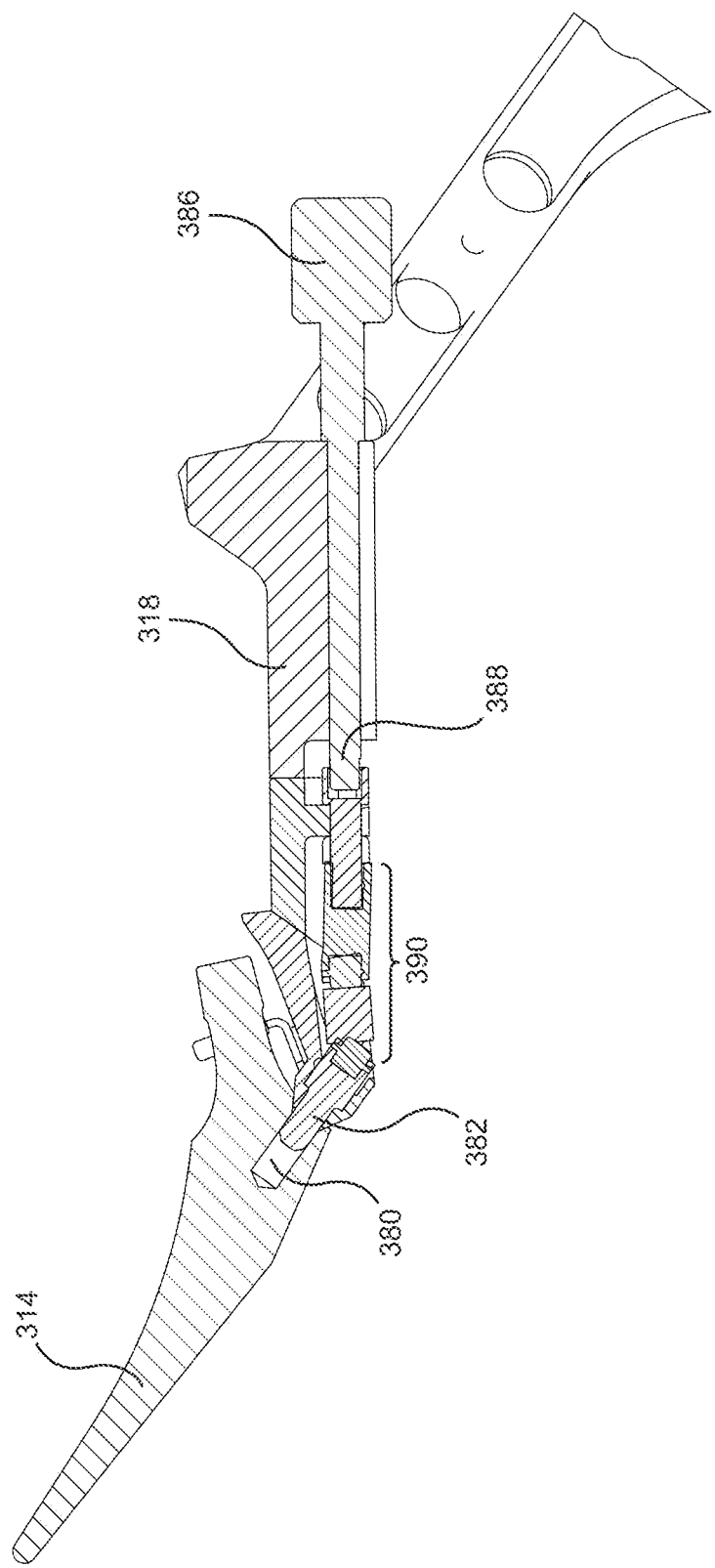
FIG. 16 is a cross-section view of an attachment mechanism adapted for use in connection with a device according to an embodiment of the present invention.

Referring now to FIGS. 15-16, an alternative embodiment of device 310 is shown in which device 310 is adapted to attach to joint implant 314. Although joint implant 314 is shown as a femoral hip stem implant, it is not limited as such. Device 10 of the present invention could be used in connection with similar procedures conducted on any joint of the body that can be replaced, including the shoulder, knee or wrist. Implant 314 shown is of the type generally used in hip replacement surgery and includes a stem section 315 and a post section 317 that is adapted to engage a ball portion (not shown) of the artificial joint typical of such an arrangement.

Implant 314 has a threaded hole 380 formed therein that is adapted to mate with a rotating threaded post 382 that is affixed to distal section 316 of handle 312. Distal section 316 has further affixed thereon a support 384 that is adapted to engage post 317 affixed to the proximal end of implant 314. In operation, threaded hole 380 is aligned with post 382 and then post 382 is turned to engage the threads between hole 380 and post 382 which draws implant 314 into contact with distal portion 316 of handle 312. Support 384 is used to restrict the rotational movement of implant 314 with respect to the handle 312 and to help maintain an appropriate position for implant 314 with respect to handle 312.

Preferably, the rotational movement of post 382 is controlled by knob 386 which extends from transition section 318 of handle 312. Knob 386 is attached to rod 388 which extends through transition section 318 toward distal section 316. Rod 388 is attached to post 382 using universal joint 390. Universal joint 390 transfers rotational motion about a longitudinal axis of rod 388 into rotational motion about a longitudinal axis of post 382 where the longitudinal axes of the respective elements are oblique relative to each other. The use of such a universal joint 390 is known in the art.

A device according to this particular embodiment of the present invention is used by selecting an appropriate femoral implant 314 and attaching that femoral implant 314 to handle 310. Then handle 312 is used to insert femoral implant 314 through an incision created during surgery and into the proximal end of the femur having been appropriately prepared to receive implant 314. Implant 314 is then aligned using handle 312 which can be aided by including a radio frequency identification (RFID) device (not shown) either in distal section 316 the handle or in implant 314. The use of RFID devices in alignment of implants and shaping instruments is known in the art. Once proper alignment is achieved, knob 386 is rotated so as to detach implant 314 from handle 312. Implant 314 is then checked for proper reduction. If necessary, handle 312 is reattached to implant 314 which can be repositioned using handle 312. Once proper reduction is achieved, handle 312 is removed from the incision and the surgery is completed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An instrument for shaping medullary canal, comprising:
(a) a handle including:
a plurality of transverse cross sections;
a first centroid located on a first cross section of the handle;
a second centroid located on a second cross section of the handle;
the first centroid and second centroid defining a handle axis;
(b) a shaping member including structure configured to shape bone, wherein the structure configured to shape bone comprises at least two cutting surfaces on opposite sides of the shaping member, the shaping member also including:
a plurality of transverse cross sections;
a third centroid located on a first cross section of the shaping member;
a fourth centroid located on a second cross section of the shaping member;
the third centroid and the fourth centroid forming a shaping member axis; and
(c) a connecting member connecting the handle and the shaping member, the connecting member having a plurality of transverse cross sections;
wherein the handle axis and the shaping member axis define a reference plane and wherein at least one centroid located on a connecting member cross section is not contained in the reference plane, wherein the connecting member comprises a dual offset including a first compound bend between the connecting member and the handle, wherein when following a direction from the connecting member to the handle, the first compound bend includes a bend in a posterior direction and a bend in a lateral direction, and wherein both bends of the first compound bend being less than 90° and wherein the connecting member includes a second compound bend between the connecting member and the shaping member, the second compound bend in an anterior and a medial direction, both compound bends being less than 90°.

* * * * *